United States Patent [19]

Ayusawa et al.

[11] Patent Number: 4,598,159

[45] Date of Patent: Jul. 1, 1986

[54] PROCESS FOR PRODUCING FURFURYLAMINE AND/OR TETRAHYDROFURFURYLAMINE

[75] Inventors: Tadashi Ayusawa; Shoichiro Mori; Tadamichi Aoki; Ryozo Hamana, all of Ibaraki, Japan

[73] Assignee: Mitsubishi Petrochemical Co., Ltd., Tokyo, Japan

[21] Appl. No.: 686,903

[22] Filed: Dec. 27, 1984

[30] Foreign Application Priority Data

Jan. 6, 1984 [JP] Japan ................. 59-581

[51] Int. Cl.⁴ ............... C07D 307/14; C07D 307/52
[52] U.S. Cl. ................................. 549/492
[58] Field of Search ........................ 549/492

[56] References Cited

U.S. PATENT DOCUMENTS

| | | | |
|---|---|---|---|
| 2,109,159 | 2/1938 | Winans | 549/492 X |
| 2,112,715 | 3/1938 | Sly | 549/492 |
| 3,812,161 | 5/1974 | Bouniot | 549/492 X |
| 4,215,073 | 7/1980 | Cornils et al. | 564/445 |

FOREIGN PATENT DOCUMENTS 26902 2/1983 Japan .

OTHER PUBLICATIONS

*Kogyo Kagaku Zasshi*, 53, 24 (1950).

*Primary Examiner*—Richard L. Raymond
*Attorney, Agent, or Firm*—Oblon, Fisher, Spivak, McClelland & Maier

[57] ABSTRACT

A process for producing furfurylamine and/or tetrahydrofurfurylamine in a high yield is disclosed, which comprises subjecting a mixture of furfural and a primary amine to a liquid-phase catalytic hydrogenation using a hydrogenation catalyst in the presence of ammonia, wherein the primary amine is furfurylamine and/or tetrahydrofurfurylamine and the hydrogenation catalyst is selected from the group consisting of cobalt-based catalysts and nickel-based catalysts.

10 Claims, 1 Drawing Figure

PROCESS FOR PRODUCING FURFURYLAMINE AND/OR TETRAHYDROFURFURYLAMINE

FIELD OF THE INVENTION

The present invention relates to a process for producing furfurylamine and/or tetrahydrofurfurylamine. According to this process, furfurylamine (hereinafter referred to as "FAM") and/or tetrahydrofurfurylamine (hereinafter referred to as "4HFAM") can be produced in high yield.

Furfurylamine and tetrahydrofurfurylamine are useful compounds as intermediates for the production of medicines, agrichemicals and fibers.

BACKGROUND OF THE INVENTION

Two basic methods are known for producing furfurylamine; one is by hydrogenation of furfural phenylhydrazone, furfural oxime, furfurylazide or furonitrile, and the other is by direct hydrogenation of furfural in the presence of ammonia. The first method by the hydrogenation of furfural derivatives requires expensive reagents in the preparation of such derivatives, and most of them involve complicated reaction steps to prepare and are difficult to handle. Therefore, the first method is not considered suitable for operation on a commercial scale.

The second method produces furfurylamine by direct hydrogenation of furfural in the presence of ammonia without forming a furfural derivative. In spite of its potential as an economical process for FAM production, the FAM yield obtained by this second method is not high.

For example, U.S. Pat. No. 2,109,159 discloses a process wherein FAM is produced by direct hydrogenation of furfural with a Raney nickel catalyst in the presence of ammonia-saturated cold ethanol. However, this method achieves 80% or less of FAM yield and produces a large amount of difurfurylamine as a by-product. A similar method is described in *KOGYO KAGAKU ZASSHI*, 53, 24 (1950), but the maximum yield of FAM is 80% and 10% or more of a high-boiling substance is produced as a by-product. According to this literature reference, it is estimated that the reaction proceeds as follows:

furfurine (whose structure shown below), at its melting point:

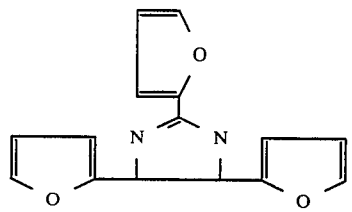

and this furfurine does not provide FAM even if it is hydrogenated. It is therefore easily understood that a drop in the selectivity for FAM will occur if the reaction temperature is 117° C. or higher. This suggests the possibility that in the one-step production of 4HFAM, hydrogenation to the tetrahydrofuran ring will not proceed smoothly in such a high temperature range.

The method shown in U.S. Pat. No. 2,112,715 produces FAM by hydrogenating furfuramide per se in an ammonia-water-methanol system, but the yield of FAM obtained is as low as 60%.

In view of the prior art techniques shown above, it is concluded that although hydrogenating furfural in the presence of ammonia would be a very interesting way to produce FAM and/or 4HFAM, the formation of furfuramide as an intermediate makes this method impracticable in industrial application because of the existence of the following disadvantages:

(1) the formation of a high-boiling substance as a by-product;

(2) the need for using a large amount of solvent; and (3) difficulty in direct formation of 4HFAM due to the upper limit on the reaction temperature.

SUMMARY OF THE INVENTION

Extensive investigations have been made to produce FAM and/or 4HFAM from furfural without using expensive reagents or fufural derivatives which are difficult to handle or prepare by overcoming the defects encountered in the conventional methods of direct hydrogenation of furfural in the presence of ammonia.

Accordingly, an object of the present invention is to provide a process for producing furfurylamine and/or

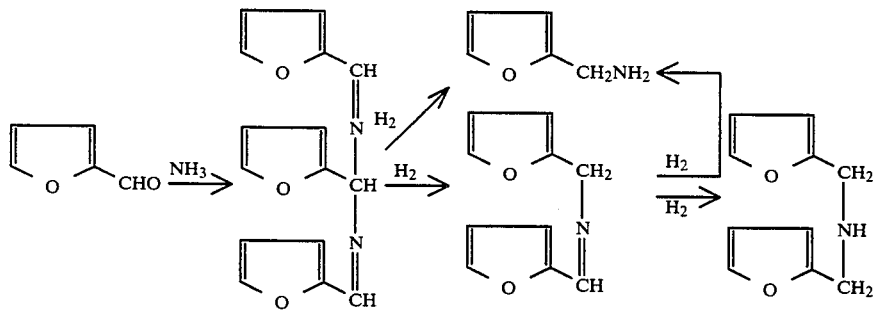

In this reaction scheme, furfural readily reacts with ammonia to form furfuramide of m.p. 117° C. Therefore, the hydrogenation reaction using furfural and ammonia requires a sufficient amount of a solvent to dissolve the furfuramide. In addition, according to U.S. Pat. No. 2,112,715, the furfuramide forms an isomer, tetrahydrofurfurylamine by liquid-phase catalytic hydrogenation of a mixture of furfural and a primary amine using a hydrogenation catalyst in the presence of ammonia, wherein the primary amine is furfurylamine and/or tetrahydrofurfurylamine and the hydrogenation catalyst is selected from the group consisting of cobalt-based catalysts and nickel-based catalysts.

BRIEF DESCRIPTION OF THE DRAWING

FIGURE is a schematic diagram of a reaction system for producing FAM by the process of the present invention in a batchwise system.

DETAILED DESCRIPTION OF THE INVENTION

Figure 1:
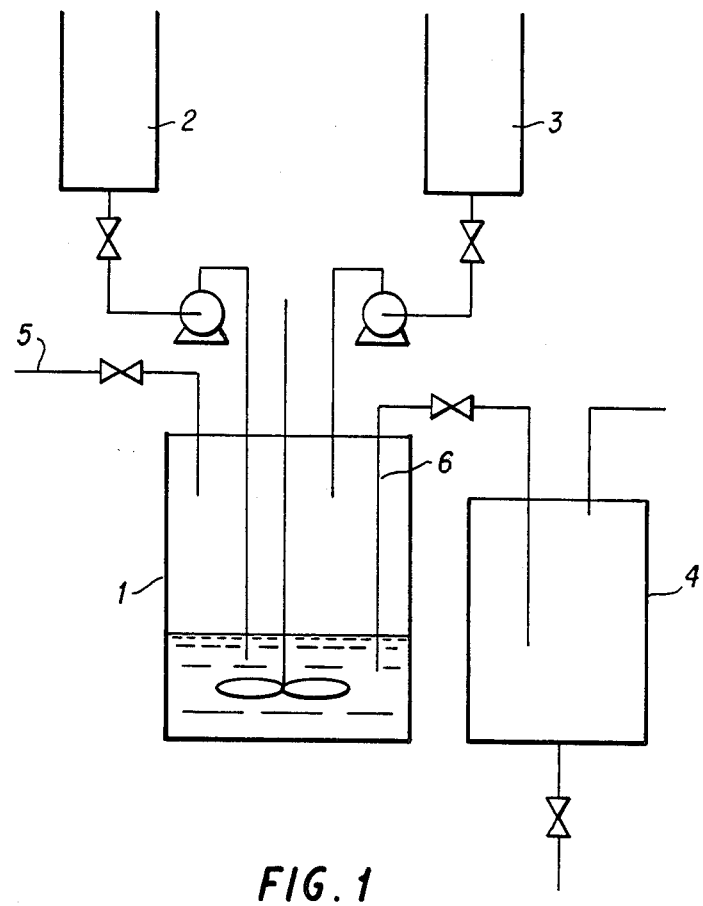

According to the process of the present invention, the defects of the prior art techniques can be eliminated: FAM can be produced almost quantitatively, and by properly selecting the reaction conditions, 4HFAM can be directly produced in one stage and in high yield. As a further advantage, either FAM or 4HFAM can be produced at a fast note.

These advantages of the present invention are hardly anticipated from the general understanding on which the conventional techniques are based. In the hydrogenation of nitrile, it is generally understood that a secondary amine is by produced as shown below:

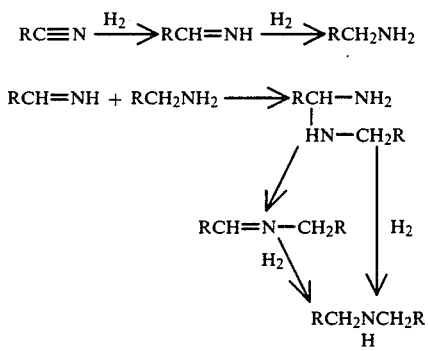

It is also known that an aldehyde compound readily reacts with a primary amine to form an azomethine compound (Schiff base), as indicated by the following reaction scheme:

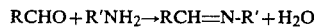

Therefore, the formation of difurfurylamine (secondary amine) as a by-product in the hydrogenation of furfural in the presence of ammonia as disclosed in U.S. Pat. No. 2,109,159 and *KOGYO KAGAKU ZASSHI*, 53, 24 (1950) suggests the occurrence of the reactions shown above.

In view of the general understanding described above, it is entirely unobvious that according to the process of the present invention, FAM and/or 4HFAM can be produced in high yield and selectivity by subjecting a mixture of furfural and a primary amine to liquid-phase catalytic hydrogenation in the presence of ammonia.

Japanese Patent Publication No. 26902/1983 shows a process for producing an aliphatic or alicyclic diamine having 4 to 18 carbon atoms, wherein an aliphatic or alicyclic dialdehyde is first reacted with a monoamine to form a diazomethine, which is then hydrogenated in the presence of ammonia to form a diamine. This method is characterized by using a straight- or branched-chain aliphatic monoamine of 3 to 13 carbon atoms as the monoamine. However, if this method is applied to the present invention, that is, if a mixture of furfural and an aliphatic amine (as the primary amine) is subjected to liquid-phase catalytic hydrogenation in the presence of ammonia, a considerable amount of a secondary amine, i.e., furfurylalkylamine, is produced as a by-product (see Comparative Example 8 described hereinafter). Therefore, the method disclosed in Japanese Patent Publication No. 26,902/1983 is inferior to the process of the present invention which can produce FAM and/or 4HFAM in a very high yield.

While palladium and other noble metal catalysts, as well as catalysts which are commonly employed in catalytic hydrogenation may be used as the catalyst in the process of the present invention, a preferred catalyst is selected from the group consisting of cobalt-based and nickel-based catalysts. Examples of cobalt- and nickel-based catalysts include Raney nickels (which may contain cocatalysts such as iron, chromium, manganese, copper, molybdenum, tungsten and rhenium) and reduced catalysts (including those which are prepared by reducing basic carbonates, hydroxides, nitrates and oxides of cobalt or nickel with hydrogen, provided that such catalysts may be supported on carriers or may contain cocatalysts of the type listed above).

According to the present invention, furfurylamine and/or tetrahydrofurfurylamine is selected as the primary amine, and after mixing this primary amine with furfural, the mixture must be subjected to liquid-phase catalytic hydrogenation in the presence of both ammonia and the catalyst specified above. The mixing ratio of furfural and FAM and/or 4HFAM is such that at least one mole of FAM and/or 4HFAM is used per mole of furfural. Preferably, 1 to 10 moles of FAM and/or 4HFAM is used per mole of furfural. If more than 10 moles of FAM and/or 4HFAM is used per mole of furfural, the yield of the final product with respect to the reactor is reduced. However, in the case of the reaction system that furfural is supplied into a reactor successively to increase the FAM yield as described hereinafter, the proportion of FAM added is not limited to the above-described ratio and even if the proportion of FAM added is greater than the above-described ratio, FAM and/or 4HFAM can be produced in a high yield without decreasing productivity.

The process of the present invention is generally performed at a reaction temperature between 0 and 300° C., preferably between about 20° and 200° C. Ammonia is used in an amount of 1 to 20 moles, preferably 1 to 10 moles, per mole of furfural. The reaction pressure that can be used in the present invention varies greatly because the vapor pressure of ammonia is highly sensitive to the amount of ammonia used and the reaction temperature. Generally, the reaction pressure ranges from 5 to 300 atm., preferably from 10 to 150 atm.

According to the process of the present invention, 4HFAM can be directly produced from furfural in a single step. However, better results are obtained by a two-step process wherein 2 to 10 moles of ammonia is first reacted with one mole of furfural at a temperature between 20° and 100° C. to form FAM, and subsequently, the hydrogen pressure is increased to at least 5 kg/cm² and the reaction temperature is elevated to between 70° and 160° C., thereby forming 4HFAM.

The catalyst is used in an amount of 0.1 to 100 wt %, preferably 0.5 to 50 wt %, based on the weight of furfural. The reaction may be performed by either a batchwise system or continuous system. In the continuous system, either a suspended bed or fixed bed may be employed.

In order to achieve an increased FAM yield in a batchwise system, a reactor containing FAM and/or 4HFAM as a reaction solvent is filled with a catalyst, ammonia and hydrogen, and after a predetermined reaction temperature is reached, furfural is fed into the reactor successively. A typical reaction system that may be used with this process is shown in FIG. 1. The system consists of a high-pressure batchwise reactor (1) which is charged with FAM and/or 4HFAM, then filled with a predetermined amount of the catalyst. After purging the reactor (1) with a gas supplied from a line (5), a predetermined amount of liquid ammonia is pumped from a vessel (2) into the reactor (1). At the same time, a predetermined amount of hydrogen gas is fed into the reactor (1) via the line (5). After the interior of the reactor (1) is set at a predetermined reaction temperature, furfural is pumped from a vessel (3) into the reactor (1) to initiate hydrogenation. As the reaction proceeds, ammonia and hydrogen are consumed to cause a pressure drop in the reactor (1). Then, corresponding amounts of liquid ammonia and hydrogen are supplied to the reactor (1). In order to complete the reaction, the reaction is usually continued from the time when the supply of furfural is finished up to the time when the reaction pressure levels off.

After the completion of the reaction, the agitation of the reaction mixture in the reactor (1) is stopped so as to settle the catalyst on the bottom of the reactor. Subsequently, the supernatant containing the product FAM is drawn into a vessel (4) through a line (6). The catalyst and part of the amine are left in the reactor (1), and after supplying additional amounts of liquid ammonia and hydrogen into the reactor, the mixture is heated to a predetermined temperature for repeating the reaction.

Typical methods for preparing the catalysts which can be used in the process of the present invention are shown below.

Preparation 1

To an aqueous solution of 150 g of cobalt nitrate $(Co(NO_3)_2.6H_2O)$ dissolved in 175 ml of distilled water, an aqueous solution of 141 g of ammonium bicarbonate $(NH_4HCO_3)$ dissolved in 650 ml of distilled water was added dropwise under agitation at 20° to 22° C. over a period of 2 hours. The resulting precipitate of basic cobalt carbonate was filtered off and thoroughly washed with distilled water to obtain a basic cobalt carbonate cake (9.09 wt % Co). To 165 g of this cake (with 15 g of Co), an aqueous solution of 1.96 g of ammonium perrhenate $(NH_4ReO_4)$ and 6.7 g of ammonium molybdenate $((NH_4)_6Mo_7O_{24})$ was added, and after thorough mixing, the obtained mixture was dried by kneading at about 80° C. The resulting powder was dried for another 12 hours at 100° to 110° C. Thereafter, the dried powder was treated in an air stream at 450° C. for 1 hr and reduced in a hydrogen stream at 300° C. for 2 hrs to obtain a cobalt-rhenium-molybdenum catalyst (atomic ratio of Co:Re:Mo=1:0.03:0.015).

Preparation 2

17 g of Raney cobalt-manganese alloy (Co:Mn:Al=30:3.5:66.5) was gradually added to 85 g of agitated 25% aqueous NaOH at room temperature so as to avoid excessive heat generation. Then, the mixture was heated at 50° C. under agitation, and after 1 hour, decantation was performed. The mixture was subjected to decantation and washing cycles with ten 200 ml portions of warm water. Subsequently, the mixture was washed with five 200 ml portions of dioxane to obtain a Raney cobalt-manganese catalyst.

Preparation 3

A Raney nickel catalyst was prepared by repeating the same procedure as in Preparation 2 above except that 10 g of Raney nickel alloy (Ni:Al=1:1) and 50 g of 25% aqueous NaOH were used.

The present invention will now be described in greater detail by reference to the following Examples and Comparative Examples.

EXAMPLE 1

A 50 cc autoclave equipped with a stirrer was charged with 0.2 g of the catalyst obtained in Preparation 1, 17.2 g of dioxane (solvent), 1.92 g of furfural feed and 1.94 g of FAM (amine). After adding 2.72 g of liquid ammonia thereto, hydrogen was introduced into the autoclave and hydrogenation was conducted for 3 hrs at 75° C. and 90 kg/cm$_2$ while the mixture was stirred at 1000 rpm. The autoclave was then cooled and the reaction product separated from the catalyst by filtration was analyzed by gas chromatography. The results are shown in Table 1.

EXAMPLE 2

Hydrogenation of furfural was conducted in the same manner as in Example 1 except that the amounts of the catalyst, dioxane, furfural, FAM and liquid ammonia were changed to 0.5 g, 9.6 g, 4.80 g, 4.85 g and 3.4 g, respectively, and the reaction pressure was reduced to 60 kg/cm$^2$. The results are shown in Table 1.

EXAMPLE 3

Hydrogenation of furfural using 4HFAM was conducted in the same manner as in Example 1 except that the amounts of the catalyst, dioxane, furfural, 4HFAM and liquid ammonia were changed to 1.0 g, 5.0 g, 4.80 g, 10.12 g and 1.1 g, respectively, and the reaction temperature, pressure and time were respectively changed to 100° C., 30 kg/cm$^2$ and 5 hrs. The results are shown in Table 1.

Comparative Example 1

The procedure of Example 1 was repeated except that no amine was used. The results are shown in Table 1.

Comparative Example 2

The procedure of Example 2 was repeated except that no amine was used and the amount of dioxane was increased to 15.0 g. The results are shown in Table 1.

Comparative Example 3

The procedure of Comparative Example 2 was repeated except that ethyl alcohol was used as the solvent in place of dioxane and the amount of liquid ammonia was reduced to 2.55 g. The results are shown in Table 1.

Comparative Example 4

The procedure of Comparative Example 3 was repeated except that the catalyst obtained in Preparation 3 was used. The results are shown in Table 1.

Comparative Example 5

The procedure of Comparative Example 1 was repeated except that the catalyst obtained in Preparation 2 was used. The results are shown in Table 1.

TABLE 1

| | | Amine | Pressure (Kg/cm$^2$) | Time (hrs) | Solvent/ furfural (weight ratio) | Ammonia/ furfural (molar ratio) | Yield per furfural feed FAM | Yield per furfural feed 4HFAM | Conversion of furfural (%) |
|---|---|---|---|---|---|---|---|---|---|
| Example | 1 | FAM | 90 | 3 | 9 | 8 | 97 | 0 | 100 |
|  | 2 | FAM | 60 | 3 | 2 | 4 | 96 | 0 | " |
|  | 3 | 4HFAM | 30 | 5 | 1 | 1.3 | 87 | 9 | " |
| Comparative | 1 | — | 90 | 3 | 9 | 8 | 88 | 0 | " |
| Example | 2 | — | 60 | 3 | 3 | 4 | 80 | 0 | " |
|  | 3 | — | 60 | 3 | 2 | 3 | 51 | 0 | " |
|  | 4 | — | 60 | 3 | 2 | 3 | 56 | 0 | " |
|  | 5 | — | 90 | 3 | 9 | 8 | 52 | 0 | " |

The above results show that the process of the present invention provides a much higher FAM and/or 4HFAM yield than the conventional method of direct hydrogenation of furfural in the presence of ammonia. A particularly advantageous feature of the present invention is that such high yields of FAM and/or 4HFAM can be achieved by using a substantially stoichiometric amount of ammonia and a small amount of solvent.

EXAMPLE 4

The procedure of Example 2 was repeated except that the amount of liquid ammonia was reduced to 1.1 g and the reaction temperature, pressure and time were increased to 150° C., 80 kg/cm$^2$ and 8 hrs, respectively. The results are shown in Table 2.

EXAMPLE 5

The procedure of Example 3 was repeated except that 0.5 g of the catalyst obtained in Preparation 3 was used and the reaction temperature and time were increased to 150° C. and 6 hrs, respectively. The results are shown in Table 2.

EXAMPLE 6

The procedure of Example 5 was repeated except that the catalyst obtained in Preparation 2 was used and the reaction pressure and time were changed to 40 kg/cm$^2$ and 4 hrs, respectively. The results are shown in Table 2.

Comparative Example 6

The procedure of Example 4 was repeated except that no amine was used, the amounts of the catalyst, furfural, dioxane and liquid ammonia were changed to 1.0 g, 9.6 g, 14.4 g and 2.2 g, respectively and the reaction time was 4 hrs. The results are shown in Table 2.

Comparative Example 7

The procedure of Comparative Example 6 was repeated except that the catalyst obtained in Preparation 3 was used and ethyl alcohol rather was used as the solvent in place of dioxane. The results are shown in Table 2.

TABLE 2

| | | Amine | Pressure (Kg/cm$^2$) | Time (hrs) | Solvent/ furfural (weight ratio) | Ammonia/ furfural (molar ratio) | Yield per furfural feed FAM | Yield per furfural feed 4HFAM | Conversion of furfural (%) |
|---|---|---|---|---|---|---|---|---|---|
| Example | 4 | FAM | 80 | 8 | 2 | 1.3 | 0 | 89 | 100 |
|  | 5 | 4HFAM | 30 | 6 | 1 | 1.3 | 1 | 89 | " |
|  | 6 | 4HFAM | 40 | 4 | 1 | 1.3 | 2 | 88 | " |
| Comparative Example | 6 | — | 80 | 4 | 1.5 | 1.8 | 25 | 29 | " |
|  | 7 | — | 80 | 4 | 1.5 | 1.8 | 6 | 45 | " |

The process of the present invention is also effective in producing 4HFAM in high yield. The conventional method of direct hydrogenation of furfural in the presence of ammonia had low selectivity for 4HFAM due to the production of an undesired high-boiling substance, and probably due to the formation of this by-product, hydrogenation of the furan ring was inhibited, giving a very low yield of the final product.

EXAMPLE 7

The procedure of Example 3 was repeated except that the reaction was carried out in two steps, the first step being performed for 5 hrs at 100° C. and 20 kg/cm$^2$, and the second step performed for 6 hrs at 150° C. and 50 kg/cm$^2$. After cooling the autoclave, the reaction product was separated from the catalyst by filtration and subjected to a gas chromatographic analysis. The yields of FAM and 4HFAM per furfural feed were 0% and 93%, respectively.

EXAMPLE 8

The procedure of Example 1 was repeated except that 0.5 g of the catalyst obtained in Preparation 1 was used; 5.0 g of dioxane (solvent), 4.8 g of furfural feed, 10.12 g of 4HFAM (molar ratio of furfural/4HFAM: 1/2 and 1.1 g of liquid ammonia (molar ratio of ammonia/furfural: 1.3) were used; and the reaction temperature, pressure and time were 100° C., 20 kg/cm$^2$ and 5 hrs, respectively. Analysis of the reaction product showed that the respective yields of FAM, 4HFAM and difurfurylamine per furfural feed were 87%, 9% and 2%.

Comparative Example 8

The procedure of Example 8 was repeated except that 10.12 g of 4HFAM was replaced by 8.71 g of n-amylamine molar ratio of furfural/n-amylamine: 1/2). Analysis of the reaction product showed that FAM, 4HFAM, difurfurylamine and n-amyl-furfurylamine were produced in respective yields of 60%, 0%, 6% and 33% per furfural feed.

EXAMPLE 9

A 300 ml stainless steel autoclave equipped with a stirrer was charged with 2.5 g of the Raney cobalt-manganese catalyst obtained in Preparation 2 and 24.3 g (0.24 mol) of tetrahydrofurfurylamin (reaction solvent). After purging the autoclave with nitrogen gas, 13.4 g (0.788 mol) of ammonia and 4 kg/cm$^2$ of hydrogen were fed into the reactor. After heating the autoclave up to 100° C., furfural was fed into the autoclave for 6 hrs at a rate of about 0.125 mol/hr. Subsequently, the reaction was continued for another 2 hours without supplying (v) On the other hand, according to the process of the present invention, the formation of by-products such as furfuryl was very slight.

After the 8 hour reaction for the FAM formation was completed, FAM hydrogenation was carried out for 6 hours at a controlled temperature of 100° C. by increasing the hydrogen pressure to 50 kg/cm$^2$. As a result, the formation of 4HFAM (0.845 mol) and the products of its consecutive reaction, piperidine and 5-aminopentanol (0.022 mol) was observed. The net yield of 4HFAM (excluding the amount initially added as the reaction solvent) was 83.3 mol % on the basis of furfural feed, and the yield of 4HFAM formed in the reaction of FAM hydrogenation was substantially quantitative.

TABLE 3

| Reactor | ← FAM formation → | | | | 4HFAM formation |
|---|---|---|---|---|---|
| Reaction time | 2 hr | 4 hr | 6 hr | 8 hr | 6 hr |
| Reaction conditions | 100° C., 30 Kg/cm$^2$ | 100° C., 12 Kg/cm$^2$ | 100° C., 5 Kg/cm$^2$ | 100° C., 5 Kg/cm$^2$ | 100° C., 50 Kg/cm$^2$ |
| Cumulative amount of furfural feed (mmol) | 257 | 525 | 753 | — | — |
| Compositions of product in the reactor (mmol) | | | | | |
| FAM | 207 | 438 | 581 | 651 | 0 |
| 4HFAM | 217 | 215 | 198 | 221 | 845 |
| Furfuryl alcohol | 37 | 47 | 51 | 49 | 53 |
| Azomethine compound I*$^1$ | 1 | 8 | 57 | 3 | 0 |
| Azomethine compound II*$^1$ | 9 | 16 | 59 | 6 | 0 |
| Hydrogenated dimer I**$^2$ | 7 | 15 | 24 | 31 | 25 |
| Hydrogenated dimer II**$^2$ | 20 | 23 | 26 | 29 | 37 |
| Furfuramine, etc. | 1 | 1 | 2 | 3 | 4 |
| Piperidine/5-aminopentanol | 0 | 0 | 0 | 0 | 22 |

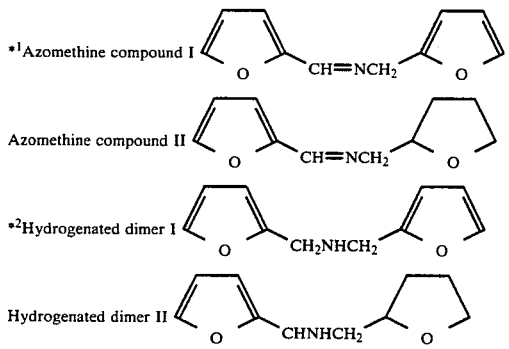

furfural until the reaction was completed. Over 8 hours of the reaction, hydrogen gas was kept supplied to compensate for the consumption that occurred during the reaction. The amount of furfural that was supplied during the first 6 hours was 0.753 mole, from which 0.651 mole of FAM was produced. Therefore, the yield of FAM on the basis of the furfural fed was 86.5 mol %. The profile of the products formed over the 8 hour reaction is shown in Table 3.

It can be apparent from the results shown in Table 3 that (i) Most of the furfural fed to the reactor was rapidly converted to FAM;

(ii) The presence of azomethine compounds considered to be an intermediate for the FAM production was observed and the FAM forming in the latter stage of the reaction took part in the formation of the azomethine compounds;

(iii) A large amount of furfuryl alcohol formed as a by-product in the initial stage of the reaction;

(iv) As another by-product, hydrogenated dimers of the azomethine compounds formed; and

EXAMPLE 10

FAM was formed by repeating the procedure of Example 9 except that 4HFAM as a reaction solvent was charged in an amount of 25.3 g (0.25 mol) and ammonia was fed in an amount of 20.4 g (1.20 mol). Furfural was fed in an amount of 0.75 mol over the first 6 hours to produce 0.671 mol of FAM, and the yield of FAM on a furfural basis was 89.5 mol %. As in Example 9, after completion of the reaction for FAM formation, the hydrogen pressure was increased to 60 kg/cm$^2$ and hydrogenation of FAM to 4HFAM was carried out. After completion of the FAM hydrogenation, the catalyst was sedimented in the autoclave and the supernatant containing the reaction product (4HFAM) was withdrawn, leaving 0.23 to 0.25 mol of 4HFAM within the autoclave. Thereafter, predetermined amounts of ammonia and hydrogen gas were fed into the autoclave and the conversion of furfural to FAM for the second time was performed using the same catalyst. The same procedure was repeated 10 times while slightly varying conditions. The results are shown in Table 4.

Except for the first batch, the FAM yields on the basis of the furfural feed were 92 to 95 mol %. This indicates the effectiveness of the present invention in FAM formation. The relatively low yield of FAM in the first batch was due to furfuryl alcohol that probably formed by hydrogenation with "occluded hydrogen" in the Raney catalyst. The fourth and tenth batches of the reaction were carried out under the same conditions. The FAM yields in the two batches were almost the same. It is concluded that there was little decrease in the activity of the Raney cobalt-manganese catalyst used.

TABLE 4

| Number of batch reactions | Reaction temperature (°C.) | $NH_3$/furfural (mol/mol) | $t_1$*(1) (hr) | $t_2$*(2) (hr) | FAM formed (mmol) | Furfuryl alcohol produced (mmol) | FAM yield (mol %) |
|---|---|---|---|---|---|---|---|
| 1 | 100 | 1.6 | 6.0 | 2.0 | 671 | 46 | 89.5 |
| 2 | 100 | 1.6 | 6.0 | 2.0 | 710 | 12 | 94.7 |
| 3 | 110 | 1.6 | 4.5 | 2.5 | 698 | 6 | 93.1 |
| 4 | 110 | 1.3 | 4.5 | 2.0 | 709 | 7 | 94.5 |
| 5 | 110 | 1.1 | 4.5 | 2.5 | 702 | 10 | 93.6 |
| 7 | 120 | 1.3 | 3.0 | 2.0 | 691 | 18 | 92.1 |
| 10 | 110 | 1.3 | 4.5 | 2.0 | 716 | 8 | 95.5 |

*(1)$t_1$: time to supply 750 mmol of furfural
*(2)$t_2$: time to complete the reaction for FAM formation after finishing the furfural supply While the invention has been described in detail and with reference to specific embodiments thereof, it will be apparent to one skilled in the art that various changes and modifications can be made therein without departing from the spirit and scope thereof.

What is claimed is:

1. A process for producing furfurylamine or tetrahydrofurfurylamine of a mixture thereof which comprises subjecting a mixture of furfural and a primary amine to a liquid-phase catalytic hydrogenation using a hydrogenation catalyst in the presence of ammonia, wherein said primary amine is furfurylamine or tetrahydrofurfurylamine or a mixture thereof, said hydrogenation catalyst is selected from the group consisting of cobalt-based catalysts and nickel-based catalysts, and wherein said hydrogenation is conducted in the presence of dioxane or in a non-solvent system, and wherein the amount of furfurylamine or tetrahydrofurfurylamine or a mixture thereof is at least one mole per mole of furfural.

2. The process of claim 1, wherein the hydrogenation catalyst is a Raney catalyst or a reduced catalyst.

3. The process of claim 1, wherein the amount of ammonia is 1 to 20 moles per mole of furfural.

4. The process of claim 1, wherein the amount of the catalyst is 0.1 to 100% by weight based on the weight of the furfural.

5. The process of claim 1, wherein the hydrogenation is conducted at a temperature of 0° to 300° C. and a pressure of 5 to 300 atms.

6. The process of claim 1, wherein a reactor containing furfurylamine or tetrahydrofurfurylamine or a mixture thereof is filled with a cobalt-based catalyst, dioxane and hydrogen, and after a predetermined reaction temperature is reached, furfural is fed into the reactor successively.

7. The process of claim 6, wherein the reaction is conducted at 20° to 200° C. under a relatively low hydrogen pressure.

8. The process for producing tetrahydrofurfurylamine of claim 1, which comprises reacting about 2 to 10 moles of ammonia with about 1 mole of furfural at a temperature of between 20° to 100° C. to form furfurylamine, and subsequently, increasing the hydrogen pressure to at least 5 kg/cm$^2$ and elevating the reaction temperature to between about 70° and 160° C., thereby forming tetrahydrofurfurylamine.

9. The process of claim 1, wherein said cobalt-based catalysts and nickel-based catalysts comprise Raney nickels which contain cocatalysts selected from the group consisting of iron, chromium, manganese, copper, molybdenum, tungsten and rhenium; and reduced catalysts prepared by reducing basic carbonates, hydroxides, nitrates and oxides of cobalt or nickel with hydrogen.

10. The process of claim 1, wherein said hydrogenation catalyst is a cobalt-based catalyst.

* * * * *